(12) United States Patent
Lam et al.

(10) Patent No.: US 6,500,855 B1
(45) Date of Patent: Dec. 31, 2002

(54) THROMBIN OR FACTOR XA INHIBITORS

(75) Inventors: Patrick Y. S. Lam, Chadds Ford, PA (US); Charles G. Clark, Cherry Hill, NJ (US); Renhau Li, Wilmington, DE (US); Donald J. P. Pinto, Kennett Square, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/033,137

(22) Filed: Jan. 2, 2002

Related U.S. Application Data

(62) Division of application No. 09/469,830, filed on Dec. 22, 1999.
(60) Provisional application No. 60/113,627, filed on Dec. 23, 1998.

(51) Int. Cl.$^7$ .................... A61K 31/406; A61K 31/405; C07D 209/02; C07D 403/00

(52) U.S. Cl. .................. 514/415; 514/422; 514/403; 514/396; 514/381; 548/483; 548/300.1; 548/356.1; 548/364.1

(58) Field of Search ................. 514/415, 422, 514/403, 396, 381; 548/483, 300.1, 356.1, 364.1

(56) References Cited

FOREIGN PATENT DOCUMENTS

EP    672658    *  9/1995

* cited by examiner

*Primary Examiner*—Mukund J. Shah
*Assistant Examiner*—Sudhaker B. Patel
(74) *Attorney, Agent, or Firm*—David H. Vance

(57) ABSTRACT

This invention relates generally to inhibitors of trypsin-like serine protease enzymes, especially factor Xa or thrombin, pharmaceutical compositions containing the same, and methods of using the same as anticoagulant agents for treatment and prevention of thromboembolic disorders.

16 Claims, No Drawings

THROMBIN OR FACTOR XA INHIBITORS

FIELD OF THE INVENTION

This invention relates generally to inhibitors of trypsin-like serine protease enzymes, especially factor Xa or thrombin, pharmaceutical compositions containing the same, and methods of using the same as anticoagulant agents for treatment and prevention of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Therefore, efficacious and specific inhibitors of factor Xa, thrombin, or both are needed as potentially valuable therapeutic agents for the treatment of thromboembolic disorders. It is thus desirable to discover new factor Xa, thrombin, or both inhibitors.

SUMMARY OF THE INVENTION

Accordingly, one object of the present invention is to provide novel nitrogen containing aromatic heterocycles, with ortho-substituted P1 groups, which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide novel compounds for use in therapy.

It is another object of the present invention to provide the use of novel compounds for the manufacture of a medicament for the treatment of thrombosis or a disease mediated by factor Xa.

DETAILED DESCRIPTION OF PREFERRED EMBODIMENTS

[1] Thus, in an embodiment, the present invention provides a novel compound selected from the group:

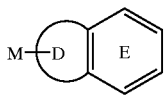

I ring D is selected from —(CH$_2$)$_3$—, —CH$_2$CH═CH—, —CH$_2$N═CH—, and a 5 membered aromatic system containing from 0–2 heteroatoms selected from the group N, O, and S, provided that from 0–1 O and S atoms are present;

ring D is substituted with 0–2 R;

E is selected from phenyl, pyridyl, pyrimidyl, pyrazinyl, and pyridazinyl, substituted with 0–1 R;

R is selected from Cl, F, Br, I, OH, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH(C$_{1-3}$ alkyl), and CH$_2$CH$_2$N(C$_{1-3}$ alkyl)$_2$;

M is selected from the group:

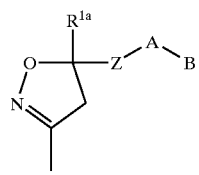

a

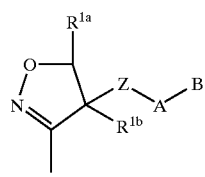

b

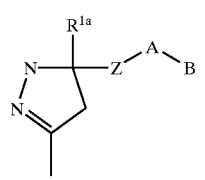

c

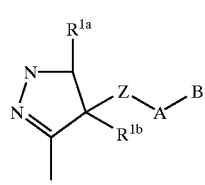

d

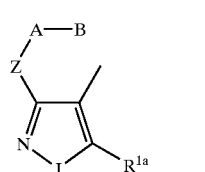

e

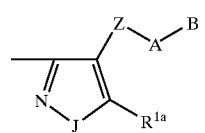

f

-continued
e 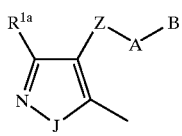
f 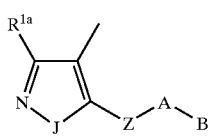
g 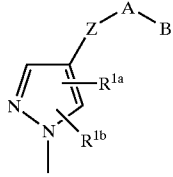
h 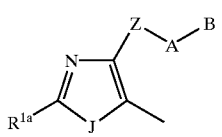
i 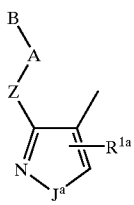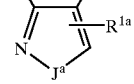
j 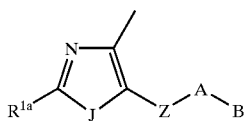
k 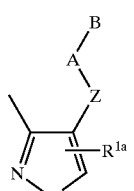
l 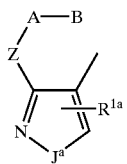
m 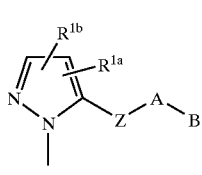
n 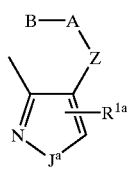
o 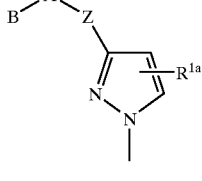
p 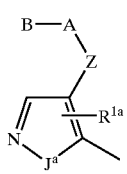
q 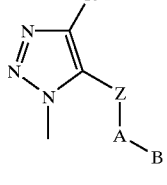
r 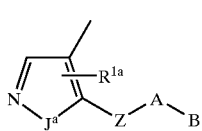
s 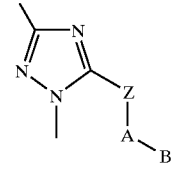
t 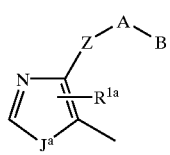
u 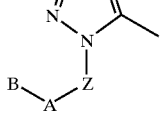
v 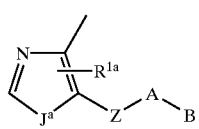

-continued
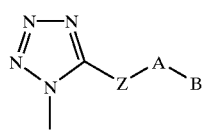
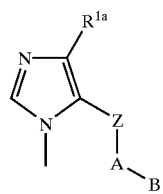
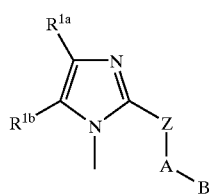
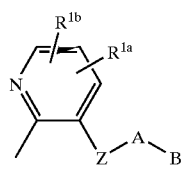
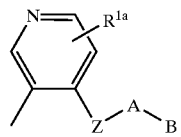
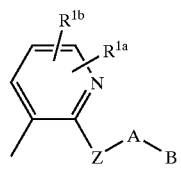
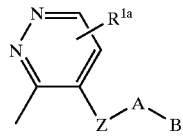
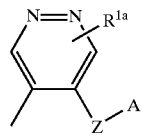
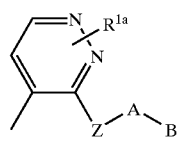
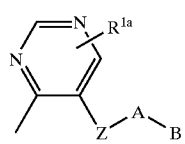
-continued
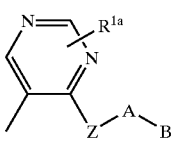 y
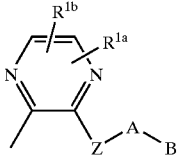 z
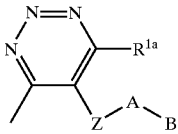 aa
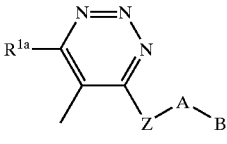 bb
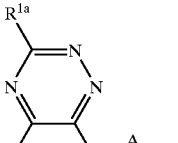 cc
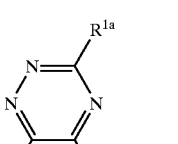 dd
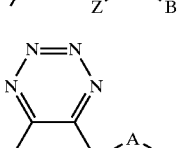 ee
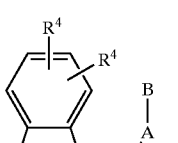 ff
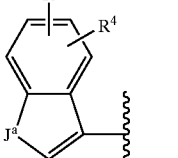 gg
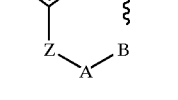 hh
ii
jj
kk
ll
mm
nn
oo
pp
qq -continued

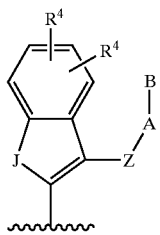
rr

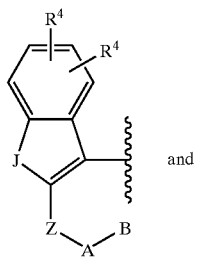
ss
and

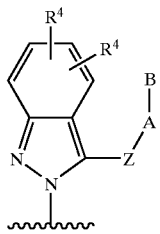
tt

J is O or S;

$J^a$ is NH or $NR^{1a}$;

Z is selected from $(CR^8R^9)_{1-4}$, $(CR^8R^9)_rO(CR^8R^9)_{r'}$, $(CR^8R^9)_rNR^3(CR^8R^9)_{r'}$, $(CR^8R^9)_rC(O)(CR^8R^9)_{r'}$, $(CR^8R^9)_rC(O)O(CR^8R^9)_{r'}$, $(CR^8R^9)_rOC(O)(CR^8R^9)_{r'}$, $(CR^8R^9)_rC(O)NR^3(CR^8R^9)_{r'}$, $(CR^8R^9)_rNR^3C(O)(CR^8R^9)_{r'}$, $(CR^8R^9)_rOC(O)O(CR^8R^9)_{r'}$, $(CH_2)_rOC(O)NR^3(CR^8R^9)_{r'}$, $(CR^8R^9)_rNR^3C(O)O(CR^8R^9)_{r'}$, $(CH_2)_rNR^3C(O)NR^3(CR^8R^9)_{r'}$, $(CR^8R^9)_rS(O)_p(CR^8R^9)_{r'}$, $(CCR^8R^9)_rSO_2NR^3(CR^8R^9)_{r'}$, $(CR^8R^9)_rNR^3SO_2(CR^8R^9)_{r'}$, and $(CR^8R^9)_rNR^3SO_2NR^3(CR^8R^9)_{r'}$, provided that Z does not form a N—N, N—O, N—S, $NCH_2N$, $NCH_2O$, or $NCH_2S$ bond with the groups to which Z is attached;

$R^{1a}$ is selected from H, $-(CH_2)_r-R^{1'}$, $-CH=CH-R^{1'}$, $NHCH_2R^{1''}$, $OCH_2R^{1''}$, $SCH_2R^{1''}$, $NH(CH_2)_2(CH_2)_tR^{1'}$, $O(CH_2)_2(CH_2)_tR^{1'}$, and $S(CH_2)_2(CH_2)_tR^{1'}$;

$R^{1'}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^{2a}$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ cycloalkylmethyl substituted with 0–2 $R^{4b}$, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$ combine to form a 5 or 6 membered saturated, partially saturated or unsaturated ring substituted with 0–2 $R^{4b}$ which contains from 0–1 additional heteroatoms selected from the group consisting of N, O, and S;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$ at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is selected from:
$C_{3-10}$ carbocyclic residue substituted with 0–2 $R^4$, and 5–10 membered heterocyclic system containing from 1–4 heteroatoms selected from the group consisting of N, O, and S substituted with 0–2 $R^4$;

B is selected from:
X—Y, $NR^2R^{2a}$, $C(=NR^2)NR^2R^{2a}$, $NR^2C(=NR^2)NR^2R^{2a}$,
$C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

X is selected from $C_{1-4}$ alkylene, $-CR^2(CR^2R^{2b})(CH_2)_t-$, $-C(O)-$, $-C(=NR^{1''})-$, $-CR^2(NR^{1''}R^2)-$, $-CR^2(OR^2)-$, $-CR^2(SR^2)-$, $-C(O)CR^2R^{2a}-$, $-CR^2R^{2a}C(O)$, $-S(O)_p-$, $-S(O)_pCR^2R^{2a}-$, $-CR^2R^{2a}S(O)_p-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from:
$(CH_2)_rNR^2R^{2a}$, provided that X—Y do not form a N—N, O—N, or S—N bond,
$C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

R⁴, at each occurrence, is selected from H, =O, (CH₂)ᵣ OR², F, Cl, Br, I, C₁₋₄ alkyl, —CN, NO₂, (CH₂)ᵣ NR²R²ᵃ, (CH₂)ᵣC(O)R²ᶜ, NR²C(O)R²ᵇ, C(O)NR²R²ᵃ, NR²C(O)NR²R²ᵃ, C(=NR²)NR²R²ᵃ, C(=NS(O)₂R⁵) NR²R²ᵃ, NHC(=NR²)NR²R²ᵃ, C(O)NHC(=NR²) NR²R²ᵃ, SO₂NR²R²ᵃ, NR²SO₂NR²R²ᵃ, NR²SO₂—C₁₋₄ alkyl, NR²SO₂R⁵, S(O)ₚR⁵, (CF₂)ᵣCF₃, NHCH₂R¹″, OCH₂R¹″, SCH₂R¹″, N(CH₂)₂(CH₂)ᵣR¹″, O(CH₂)₂(CH₂)ᵣR¹″, and S(CH₂)₂(CH₂)ᵣR¹″, alternatively, one R⁴ is a 5–6 membered aromatic heterocycle containing from 1–4 heteroatoms selected from the group consisting of N, O, and S;

R⁴ᵃ, at each occurrence, is selected from H, =O, (CH₂)ᵣ OR², (CH₂)ᵣ—F, (CH₂)ᵣ—Br, (CH₂)ᵣ—Cl, Cl, Br, F, I, C₁₋₄ alkyl, —CN, NO₂, (CH₂)ᵣNR²R²ᵃ, (CH₂)ᵣC(O) R²ᶜ, NR²C(O)R²ᵇ, C(O)NR²R²ᵃ, C(O)NH(CH₂)₂ NR²R²ᵃ, NR²C(O)NR²R²ᵃ, C(=NR²)NR²R²ᵃ, NHC (=NR²)NR²R²ᵃ, SO₂NR²R²ᵃ, NR²SO₂NR²R²ᵃ, NR²SO₂—C₁₋₄ alkyl, C(O)NHSO₂—C₁₋₄ alkyl, NR²SO₂R⁵, S(O)ₚR⁵, and (CF₂)ᵣCF₃;

alternatively, one R⁴ᵃ is a 5–6 membered aromatic heterocycle containing from 1–4 heteroatoms selected from the group consisting of N, O, and S substituted with 0–1 R⁵;

R⁴ᵇ, at each occurrence, is selected from H, =O, (CH₂)ᵣ OR³, F, Cl, Br, I, C₁₋₄ alkyl, —CN, NO₂, (CH₂)ᵣ NR³R³ᵃ, (CH₂)ᵣC(O)R³, (CH₂)ᵣC(O)OR³ᶜ, NR³C(O) R³ᵃ, C(O)NR³R³ᵃ, NR³C(O)NR³R³ᵃ, C(=NR³) NR³R³ᵃ, NR³C(=NR³)NR³R³ᵃ, SO₂NR³R³ᵃ, NR³SO₂NR³R³ᵃ, NR³SO₂—C₁₋₄ alkyl, NR³SO₂CF₃, NR³SO₂—phenyl, S(O)ₚCF₃, S(O)ₚ—C₁₋₄ alkyl, S(O)ₚ-phenyl, and (CF₂)ᵣCF₃;

R⁵, at each occurrence, is selected from CF₃, C₁₋₆ alkyl, phenyl substituted with 0–2 R⁶, and benzyl substituted with 0–2 R⁶;

R⁶, at each occurrence, is selected from H, OH, (CH₂)ᵣ OR², halo, C₁₋₄ alkyl, CN, NO₂, (CH₂)ᵣNR²R²ᵃ,(CH₂)ᵣ C(O)R²ᵇ, NR²C(O)R²ᵇ, NR²C(O)NR²R²ᵃ, C(=NH) NH₂, NHC(=NH)NH₂, SO₂NR²R²ᵃ, NR²SO₂NR²R²ᵃ, and NR²SO₂C₁₋₄ alkyl;

R⁷, at each occurrence, is selected from H, OH, C₁₋₆ alkyl, C₁₋₆ alkylcarbonyl, C₁₋₆ alkoxy, C₁₋₄ alkoxycarbonyl, (CH₂)ₙ-phenyl, C₆₋₁₀ aryloxy, C₆₋₁₀ aryloxycarbonyl, C₆₋₁₀ arylmethylcarbonyl, C₁₋₄ alkylcarbonyloxy C₁₋₄ alkoxycarbonyl, C₆₋₁₀ arylcarbonyloxy C₁₋₄ alkoxycarbonyl, C₁₋₆ alkylaminocarbonyl, phenylaminocarbonyl, and phenyl C₁₋₄ alkoxycarbonyl;

R⁸, at each occurrence, is selected from H, C₁₋₆ alkyl and (CH₂)ₙ-phenyl;

alternatively, R⁷ and R⁸ combine to form a 5 or 6 membered saturated, ring which contains from 0–1 additional heteroatoms selected from the group consisting of N, O, and S;

R⁹, at each occurrence, is selected from H, C₁₋₆ alkyl and (CH₂)ₙ-phenyl;

n, at each occurrence, is selected from 0, 1, 2, and 3;

m, at each occurrence, is selected from 0, 1, and 2;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0, 1, 2, and 3.

[2] In another embodiment, the present invention provides a novel compound selected from the group:

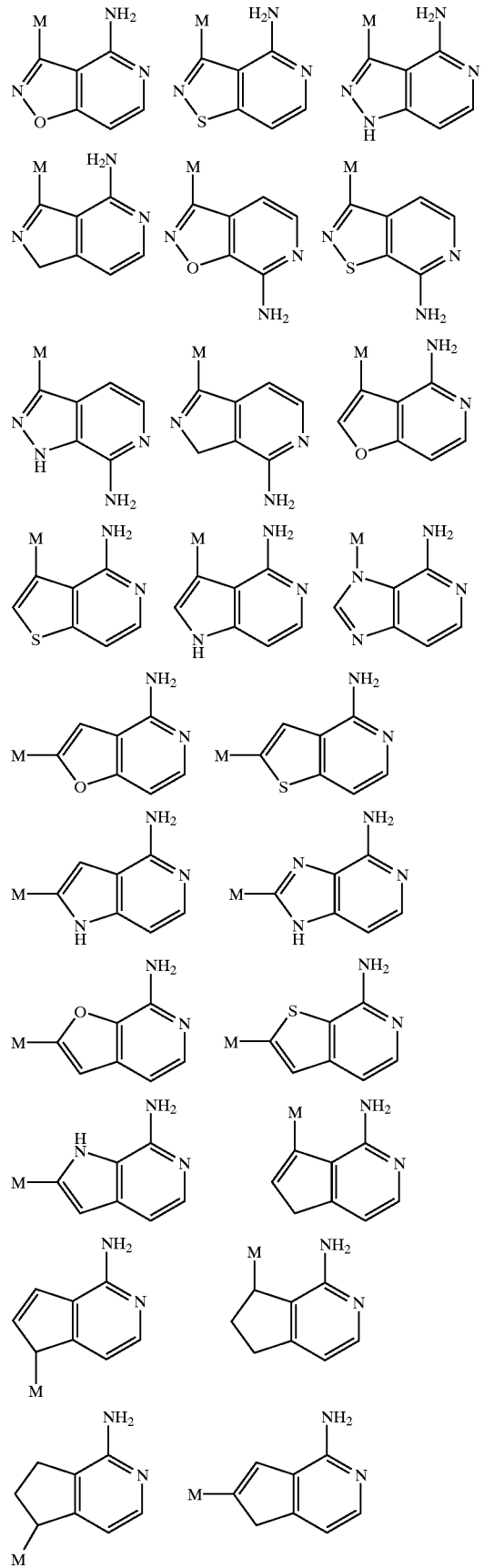

-continued

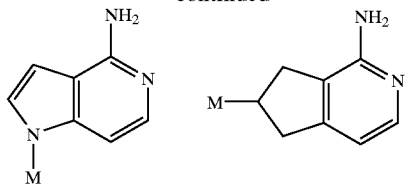

wherein,

M is selected from the group:

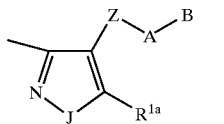 f

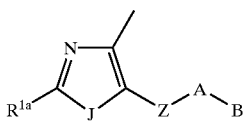 j

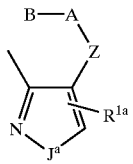 l

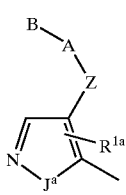 m

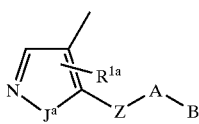 n

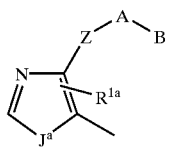 o

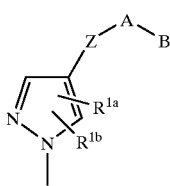 q

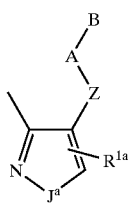 s

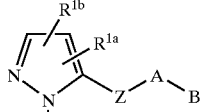 t

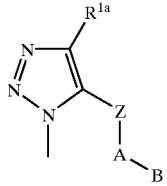 v

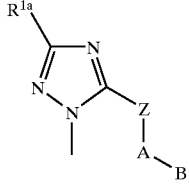 w and

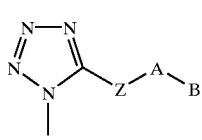 y

R is selected from H, Cl, F, Br, I, $(CH_2)_rOR^3$, $C_{1-4}$ alkyl, $OCF_3$, $CF_3$, $C(O)NR^7R^8$, and $(CR^8R^9)_rNR^7R^8$;

Z is selected from $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$, $SO_2NH$, and $NHSO_2$, provided that Z does not form a N—N, N—O, $NCH_2N$, or $NCH_2O$ bond with ring M or group A;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, irnidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: H, Y, and X—Y;

X is selected from $C_{1-4}$ alkylene, —C(O)—, —C(=NR)—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is $NR^2R^{2a}$ or $CH_2NR^2R^{2a}$, provided that X—Y do not form a N—N or O—N bond;

alternatively, Y is selected from one of the following carbocyclic and heterocyclic systems which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

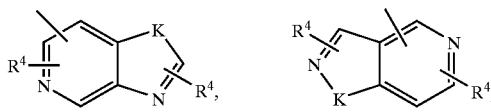
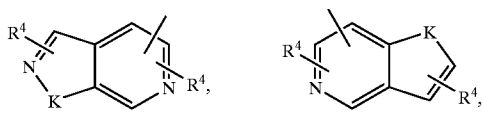
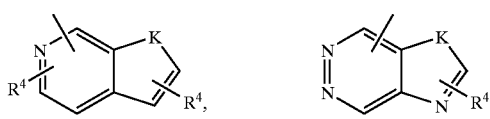
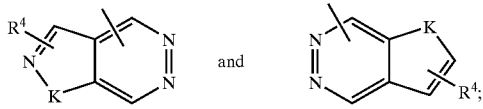

and

K is selected from O, S, NH, and N.

[3] In another embodiment, the present invention provides a novel compound selected from the group:

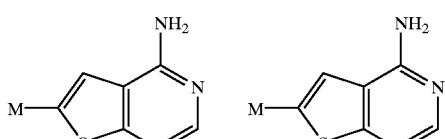
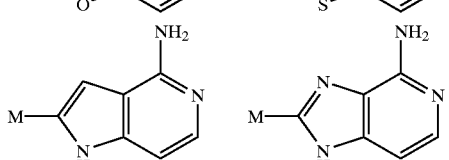
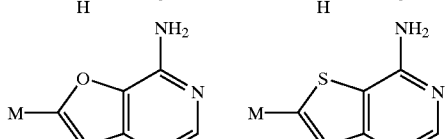
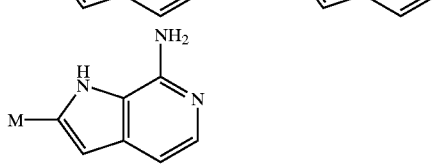

M is selected from the group:

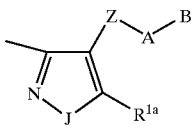

f

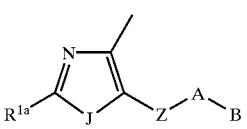

j

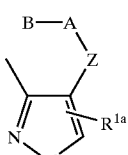

l

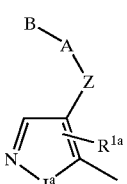

m

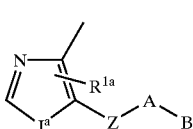

n

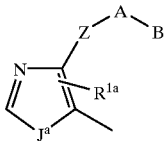

o

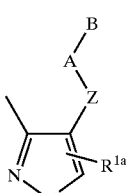

s

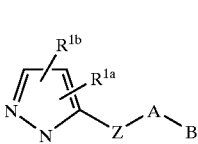

t

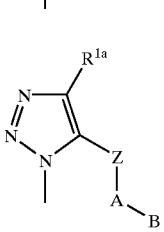

v

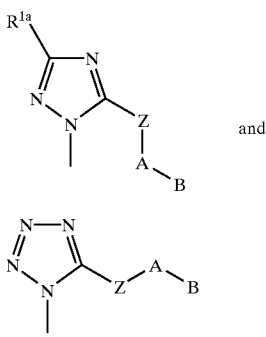

w and y

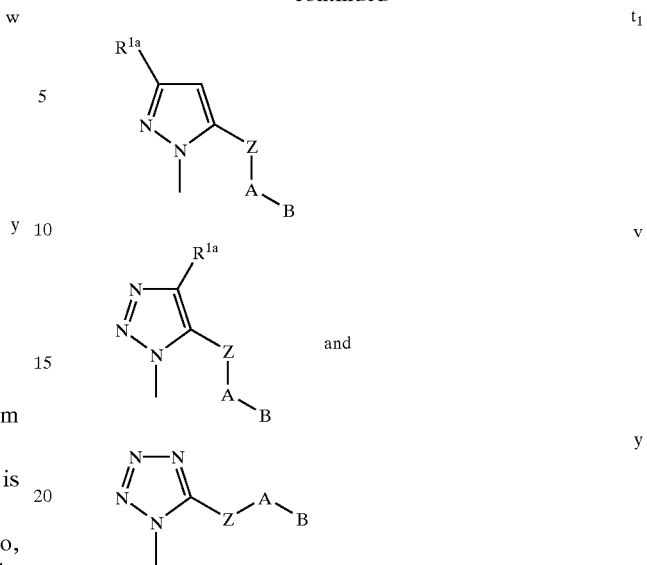

Z is C(O)CH$_2$ and CONH, provided that Z does not form a N—N bond with group A;

A is selected from phenyl, pyridyl, and pyrimidyl, and is substituted with 0–2 R$^4$; and, B is selected from Y, X—Y, phenyl, pyrrolidino, morpholino, 1,2,3-triazolyl, and imidazolyl, and is substituted with 0–1 R$^{4a}$;

B is selected from: Y and X—Y;

X is selected from CH$_2$, —C(O), and O;

Y is NR$^2$R$^{2a}$ or CH$_2$NR$^2$R$^{2a}$, provided that X—Y does not form an O—N bond;

alternatively, Y is selected from one of the following carbocyclic and heterocyclic systems which are substituted with 0–2 R$^{4a}$;
  phenyl, piperazinyl, pyridyl, pyrimidyl, morpholinyl, pyrrolidinyl, imidazolyl, and 1,2,3-triazolyl;

R$^2$, at each occurrence, is selected from H, CF$_3$, CH$_3$, benzyl, and phenyl;

R$^{2a}$, at each occurrence, is selected from H, CF$_3$, CH$_3$, CH(CH$_3$)$_2$, cyclopropylmethyl, benzyl, and phenyl;

alternatively, R$^2$ and R$^{2a}$ combine to form a ring system substituted with 0–2 R$^{4b}$, the ring system being selected from pyrrolidinyl, piperazinyl and morpholino;

R$^4$, at each occurrence, is selected from OH, (CH$_2$)$_r$OR$^2$, Cl, F, C$_{1-4}$ alkyl, (CH$_2$)$_r$NR$^2$R$^{2a}$, and (CF$_2$)$_r$CF$_3$;

R$^{4a}$ is selected from Cl, F, C$_{1-4}$ alkyl, CF$_3$, (CH$_2$)$_r$NR$^2$R$^{2a}$, S(O)$_p$R$^5$, SO$_2$NR$^2$R$^{2a}$, and 1-CF$_3$-tetrazol-2-yl;

R$^{4b}$, at each occurrence, is selected from OH, Cl, F, CH$_3$, and CF$_3$;

R$^5$, at each occurrence, is selected from CF$_3$, C$_{1-6}$ alkyl, phenyl, and benzyl;

R$^7$, at each occurrence, is selected from H, CH$_3$, and CH$_2$CH$_3$; and,

R$^8$, at each occurrence, is selected from H and CH$_3$.

[4] In another embodiment, the present invention provides a novel compound wherein:

M is selected from the group:

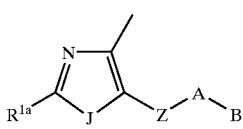

j

J is N;

R$^{1a}$ is absent or is —(CH$_2$)$_r$-R$^{1'}$;

R$^{1'}$ is selected from H, C$_{1-3}$ alkyl, F, Cl, —CN, CF$_3$, (CH$_2$)$_r$OR$^2$, NR$^2$R$^{2a}$, C(O)R$^{2c}$, OC(O)R$^2$, S(O)$_p$R$^{2b}$, NR$^2$C(O)R$^{2b}$, C(O)NR$^2$R$^{2a}$, SO$_2$NR$^2$R$^{2a}$, C$_{3-6}$ carbocyclic residue substituted with 0–2 R$^{4a}$, and 5–6 membered heterocyclic system containing from 1–4 heteroatoms selected from the group consisting of N, O, and S substituted with 0–2 R$^{4a}$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-CF$_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 2-(N,N-dimethylaminomethyl)phenyl, 2-(isopropylaminomethyl)phenyl, 2-(cyclopropylaminomethyl)phenyl, 2-(N-pyrrolidinylmethyl)phenyl, 2-(3-hydroxy-N-pyrrolidinylmethyl)phenyl, 4-morpholino, 2-(1'-CF$_3$-tetrazol-2-yl)phenyl, 4-morpholinocarbonyl, 1-methyl-2-imidazolyl, 2-methyl-1-imidazolyl, 5-methyl-1-imidazolyl, 2-(N,N-dimethylaminomethyl)imidazolyl, 2-methylsulfonyl-1-imidazolyl and, 5-methyl-1,2,3-triazolyl.

In another embodiment, the present invention provides novel pharmaceutical compositions, comprising: a pharmaceutically acceptable carrier and a therapeutically effective amount of a compound of present invention or a pharmaceutically acceptable salt form thereof.

In another embodiment, the present invention provides a novel method for treating or preventing a thromboembolic disorder, comprising: administering to a patient in need thereof a therapeutically effective amount of a compound of the present invention or a pharmaceutically acceptable salt form thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic group" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotarns independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro

[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit factor Xa or thrombin or treat diseases related to factor Xa or thrombin in a host. The combination of compounds is preferably a synergistic combination. Synergy, as described for example by Chou and Talalay, Adv. Enzyme Regul. 22:27–55 (1984), occurs when the effect (in this case, inhibition of factor Xa or thrombin) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991). All references cited herein are hereby incorporated in their entirety herein by reference.

Compounds wherein rings D—E are A or B, shown below:

A

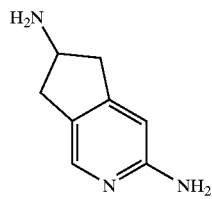

B can be prepared via the methodology outlined in Scheme I below.

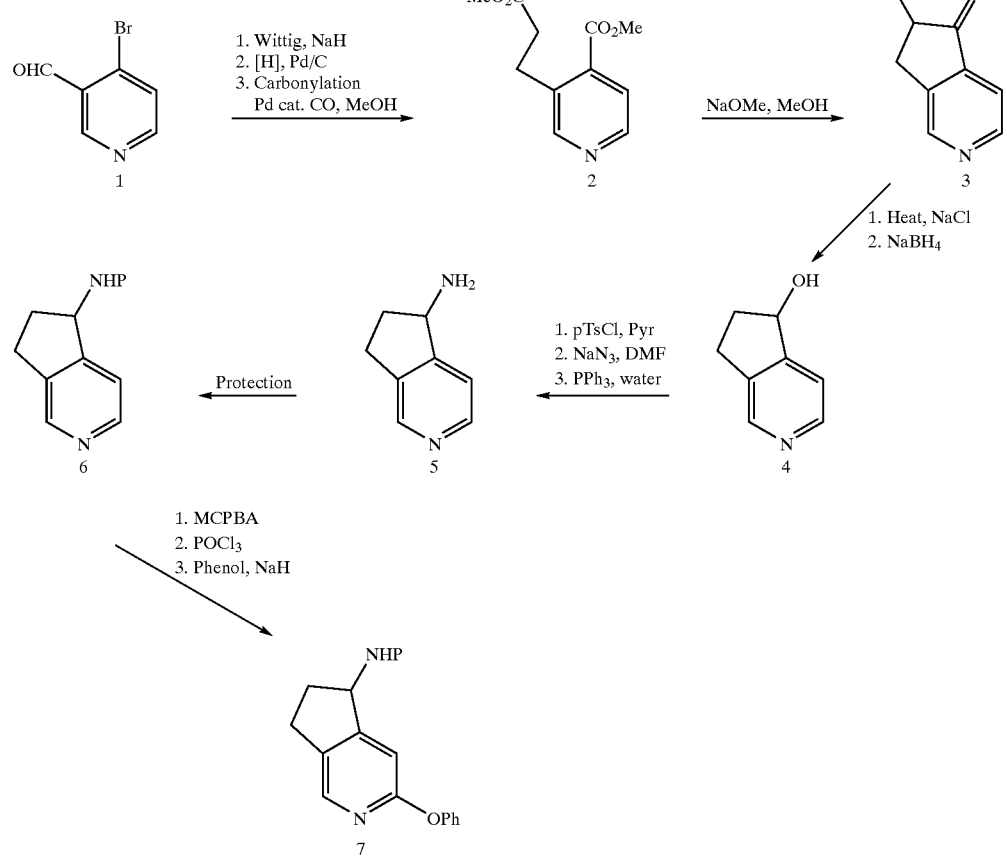

Removal of the amino protecting group followed by further manipulation can afford key starting materials wherein the amino is a benzylamine or alpha-amino acid or all analogs stated earlier. The starting material can also be obtained from intermediate 4 via an SN2 type displacement of the o-tosylate. Decarboxylation of intermediate 3 affords the ketone analog that also can be further manipulated to afford additional starting materials D—E. Coupling of analogs such as intermediate 7 via standard techniques followed by displacement of the phenoxy pyridine via standard techniques known to those in the art should afford the compounds of formula A. Chiral compounds can be separated via chiral HPLC techniques or by co-crystallization methods with a known chiral precursor.

Compounds wherein D—E is of formula B as shown above can be prepared as shown in Scheme II.

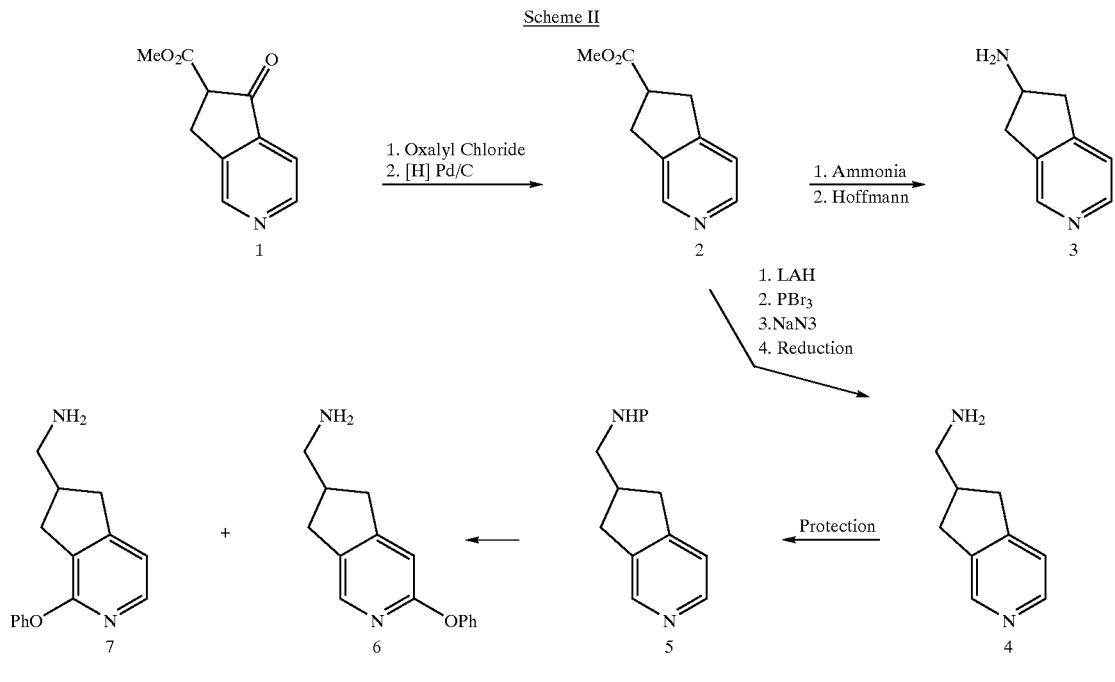

Via this scheme amino intermediates such as 3(B) and phenoxy analogs 6 and 7 can be obtained easily via the methods previously described. These intermediates can be further coupled to requisite precursors followed by conversion of the phenoxy group to an amino via standard techniques to afford the amino-pyridyl compounds of formula 1–3.

The unsaturated analogs can be prepared according to Scheme III.

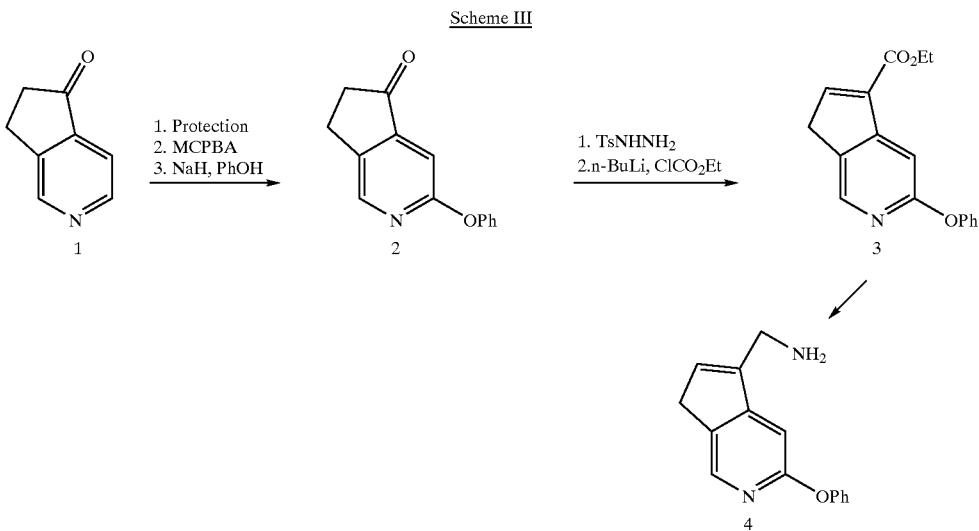

Intermediate 3 can be further manipulated to afford other D—E intermediates via methods described previously. In a similar fashion the other unsaturated analog can be prepared via Scheme IV shown below.

Scheme IV

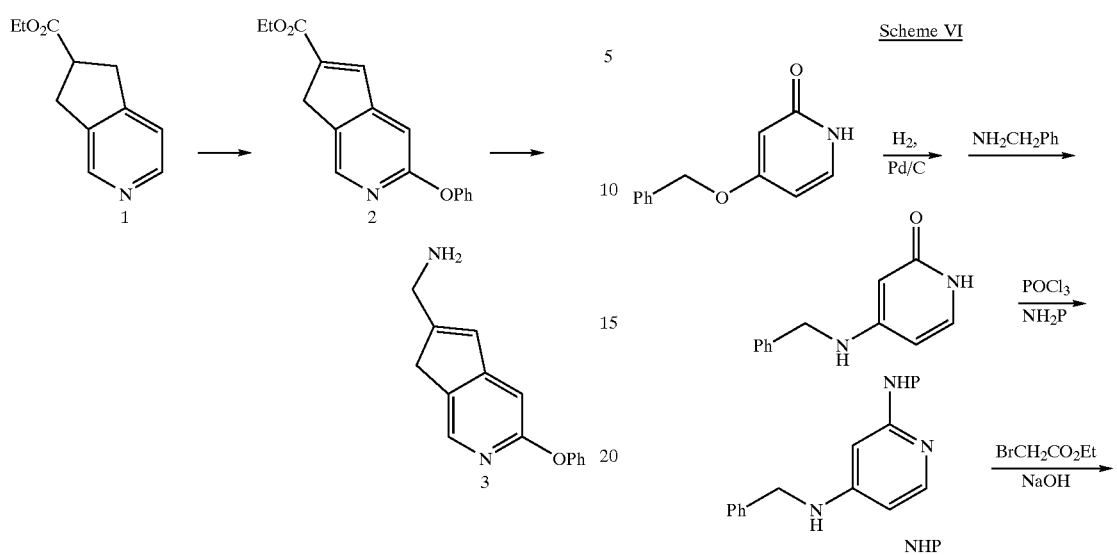

Scheme V describes the preparation of 3-aminobenzofuran intermediates.

Scheme VI describes the preparation of indole intermediates.

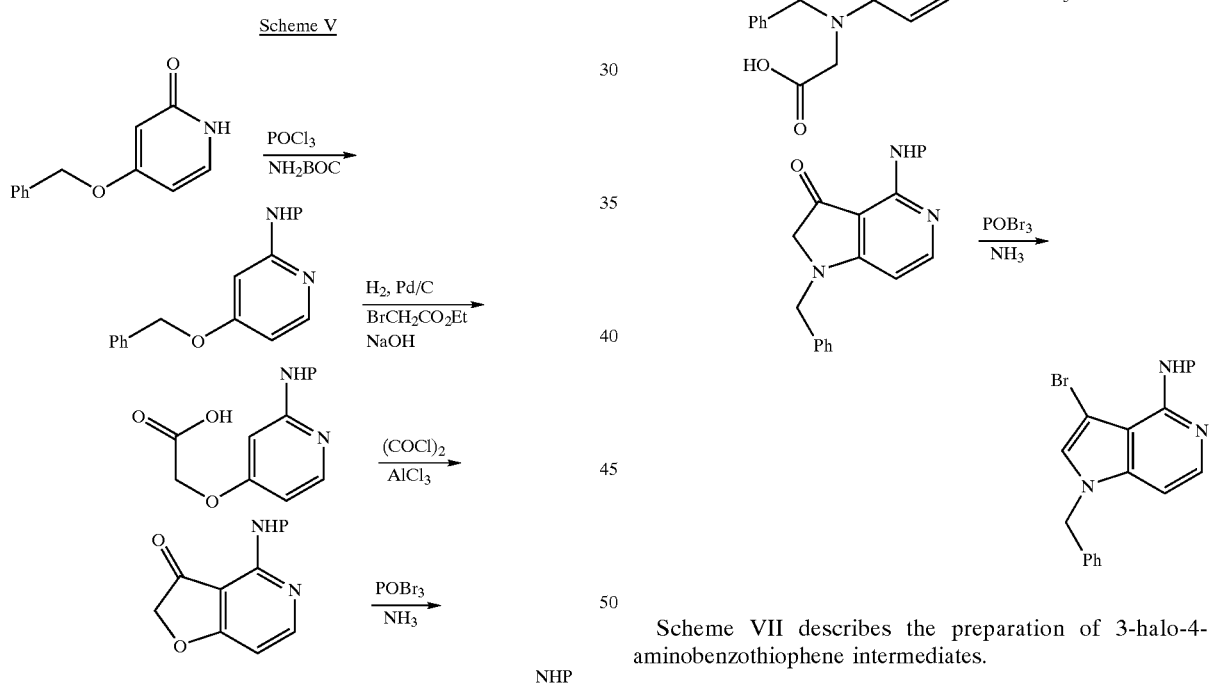

4-benzyloxy-2(1H)-pyridone (available from Aldrich) can be converted to the aminopyridine derivative using standard procedures known to the practitioners of the art. Debenzylation, coupling with bromoethylacetate, followed by basic hydrolysis affords an intermediate that undergoes the Friedel-Crafts acylation.

Scheme VII describes the preparation of 3-halo-4-aminobenzothiophene intermediates.

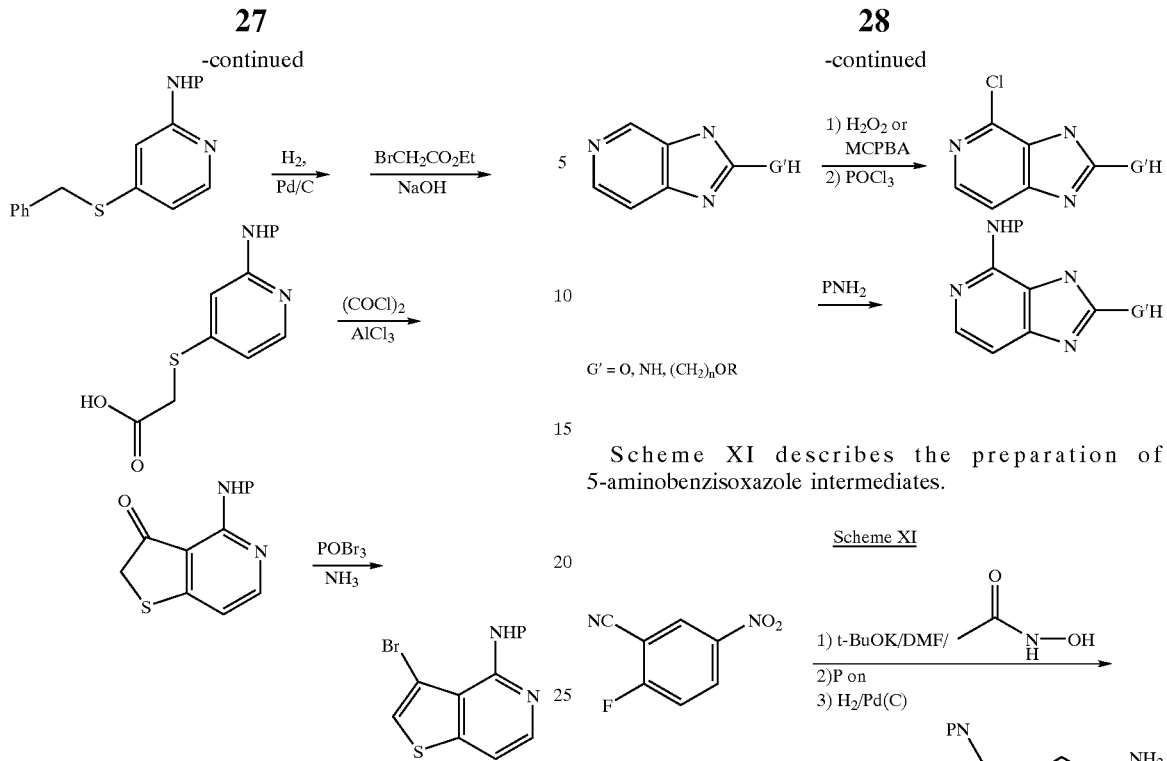

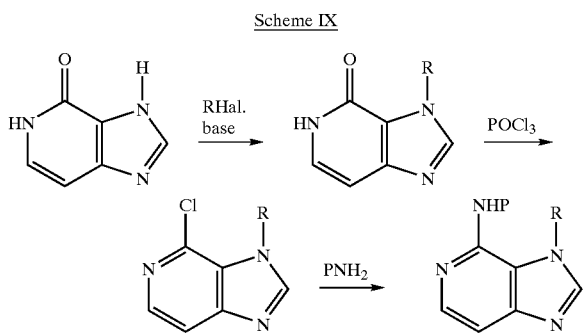

Scheme VIII describes the preparation of 1-substituted-7-amino-azabenzimidazole intermediates.

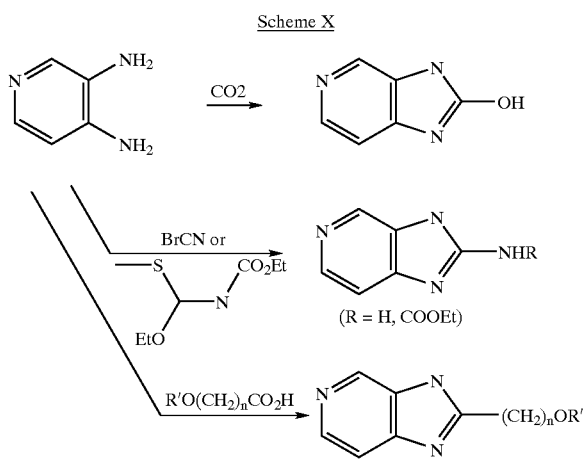

Scheme X describes the preparation of 2-substituted-7-amino-azabenzimidazole intermediates.

Scheme XI describes the preparation of 5-aminobenzisoxazole intermediates.

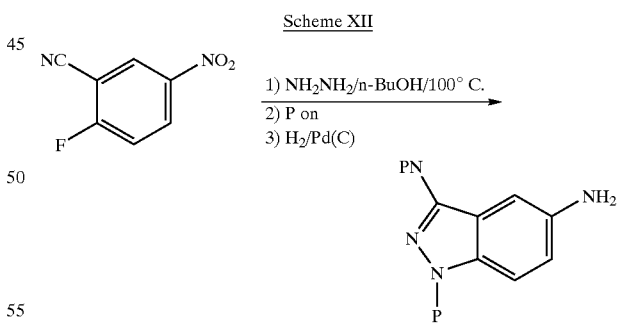

Synthesis of 5-aminobenzisoxazoles in which the 3-position may be a protected amine could be accomplished starting from the commercially available 3-cyano4-fluoronitrobenzene. Displacement of flourine with acetohydroxamic acid under basic conditions followed by ring closure by subsequent addition to the nitrile would yield the benzisoxazole core. Suitable protection and reduction of the aryl nitro group would provide the desired compound.

Scheme XII describes the preparation of 5-aminoindazole intermediates.

Synthesis of 5-aminoindazoles in which the 3-position may be a protected amine could be accomplished starting from the commercially available 3-cyano4-fluoronitrobenzene. Displacement of flourine with hydrazine followed by ring closure by subsequent addition to the nitrile would yield the indazole core. Suitable protection and reduction of the aryl nitro group would provide the desired compound.

Scheme XIII describes the preparation of 5-aminobenzisothiazole intermediates.

Scheme XIII

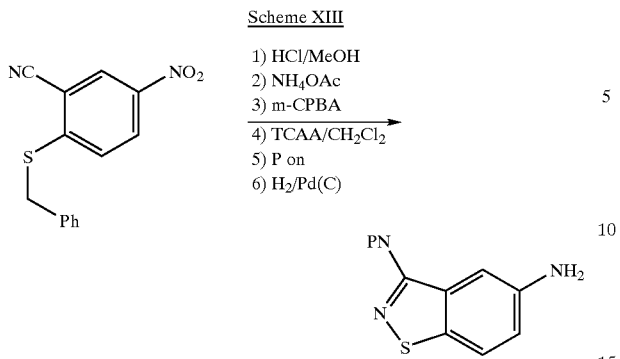

1) HCl/MeOH
2) NH₄OAc
3) m-CPBA
4) TCAA/CH₂Cl₂
5) P on
6) H₂/Pd(C)

Synthesis of 5-aminobenzisothiazoles in which the 3-position may be a protected amine could be accomplished starting from the commercially available 2-benzylthio-5-nitrobenzonitrile. Conversion of the aryl nitrile to benzamidine, sulfoxide formation and ring closure/debenzylation would yield the benzisothiazole core. Suitable protection and reduction of the aryl nitro group would provide the desired compound.

Scheme XIV describes the preparation of 6-aminobenzisoxazoleintermediates.

Scheme XIV

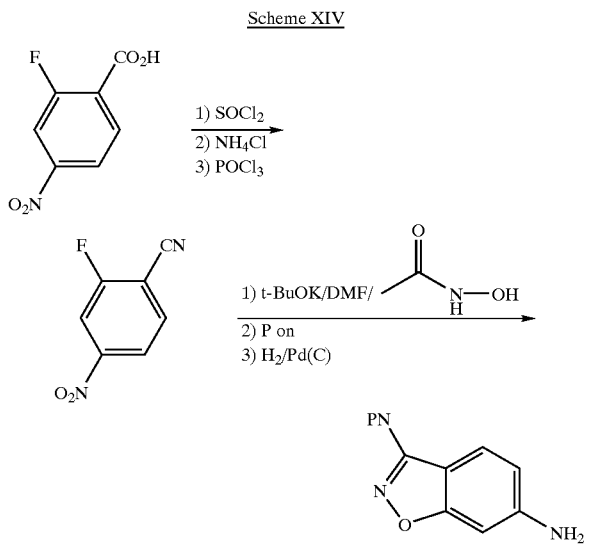

1) SOCl₂
2) NH₄Cl
3) POCl₃

1) t-BuOK/DMF/ acetohydroxamic acid
2) P on
3) H₂/Pd(C)

Synthesis of 6-aminobenzisoxazoles in which the 3-position may be a protected amine could be accomplished starting from commercially available 2-fluoro-4-nitrobenzoic acid. Conversion of carboxylic acid to nitrile via standard manipulations would give 2-fluoro-4-nitrobenzonitrile. Displacement of flourine with acetohydroxamic acid under basic conditions followed by ring closure by subsequent addition to the nitrile would yield the benzisoxazole core. Suitable protection and reduction of the aryl nitro group would provide the desired compound.

Scheme XV describes the preparation of 5-aminoindazole intermediates.

Scheme XV

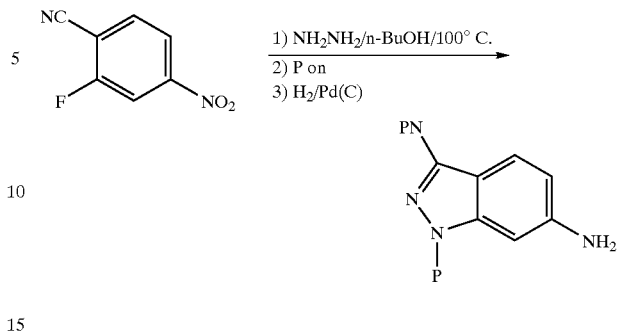

1) NH₂NH₂/n-BuOH/100° C.
2) P on
3) H₂/Pd(C)

Synthesis of 5-aminoindazoles in which the 3-position may be a protected amine could be accomplished starting from from 2-fluoro-4-nitrobenzonitrile whose synthesis is described elsewhere in this patent. Displacement of flourine with hydrazine followed by ring closure by subsequent addition to the nitrile would yield the indazole core. Suitable protection and reduction of the aryl nitro group would provide the desired compound.

Scheme XVI describes the preparation of 6-aminobenzisothiazole intermediates.

Scheme XVI

PhCH₂SH / NaH/DMF

1) HCl/MeOH
2) NH₄OAc
3) m-CPBA
4) TCAA/CH₂Cl₂
5) P on
6) H₂/Pd(C)

Synthesis of 6-aminobenzisothiazoles in which the 3-position may be a protected amine could be accomplished starting from 2-fluoro-4-nitrobenzonitrile whose synthesis is described elsewhere in this patent. Displacement of flourine with benzylthio anion yields 2-benzylthio-4-nitrobenzonitrile. Conversion of the aryl nitrile to benzamidine, sulfoxide formation and ring closure/debenzylation would yield the benzisothiazole core. Suitable protection and reduction of the aryl nitro group would provide the desired compound.

Scheme XVII describes the preparation of 6-aminoisoindole intermediates.

Scheme XVII

1) NBS
2) NaN₃/PhCH₃
3) Ph₃P/THF/H₂O
4) HCl/EtOH
5) P on
6) SnCl₂

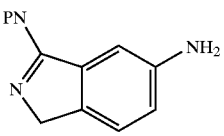

Synthesis of 6-aminoisoindoles in which the 1-position may be a protected amine could be accomplished starting from commercially available 2-cyano4-nitrotoluene. Bromination of tolyl methyl to give a benzyl bromide followed by displacement with azide and reduction to benzylamine would cyclize to the isoindole core. Suitable protection and reduction of the aryl nitro group would provide the desired compound.

Scheme XVIII describes the preparation of 5-aminoisoindole intermediates.

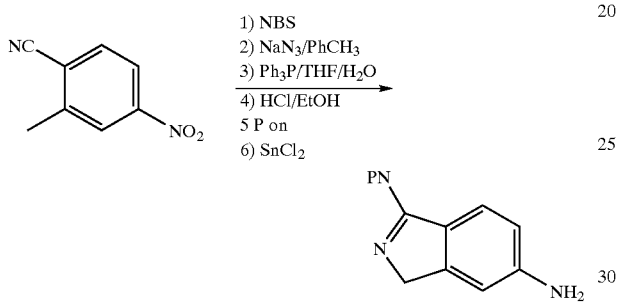

Scheme XVIII

1) NBS
2) NaN$_3$/PhCH$_3$
3) Ph$_3$P/THF/H$_2$O
4) HCl/EtOH
5 P on
6) SnCl$_2$

Synthesis of 5-aminoisoindoles in which the 1-position may be a protected amine could be accomplished starting from commercially available 2-cyano-5-nitrotoluene. Bromination of tolyl methyl to give a benzyl bromide followed by displacement with azide and reduction to benzylamine would cyclize to the isoindole core. Suitable protection and reduction of the aryl nitro group would provide the desired compound.

Scheme XIX describes the preparation of 2-aminoindole derivatives a intermediates.

Scheme XIX

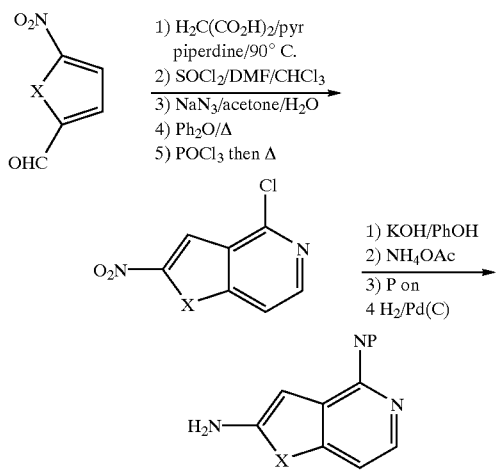

1) H$_2$C(CO$_2$H)$_2$/pyr piperdine/90° C.
2) SOCl$_2$/DMF/CHCl$_3$
3) NaN$_3$/acetone/H$_2$O
4) Ph$_2$O/Δ
5) POCl$_3$ then Δ

1) KOH/PhOH
2) NH$_4$OAc
3) P on
4 H$_2$/Pd(C)

X = O, S

Synthesis of the desired compounds in which the 4-position may be a protected amine could be accomplished starting from the commercially available furan or thiophene. Using literature methods (J. Med. Chem. 1989, 32, 1147) one could obtain the 2-nitro-4-chloro-furo or thieno<3,2-c>pyridine. Displacement of the 4-chloro with phenoxide then conversion to 4-amino followed by suitable protection and reduction of the aryl nitro group would provide the desired compound.

Scheme XX describes the preparation of 2-amino-1-H-pyrrolo[3,2-c]pyridine intermediates.

Scheme XX

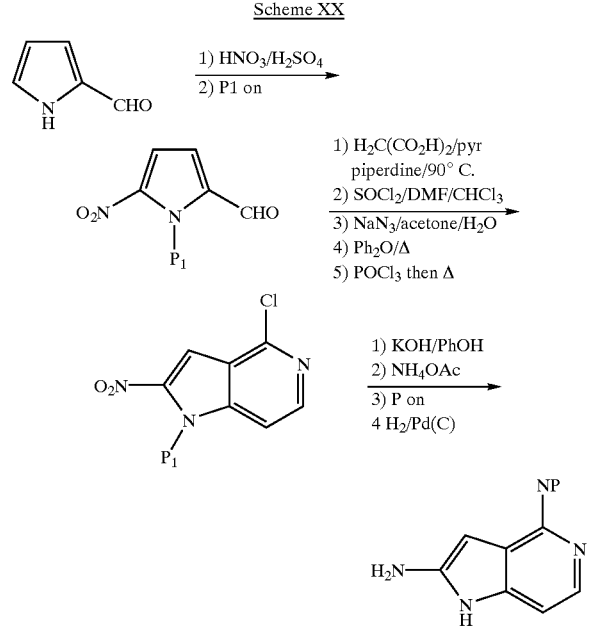

1) HNO$_3$/H$_2$SO$_4$
2) P1 on

1) H$_2$C(CO$_2$H)$_2$/pyr piperdine/90° C.
2) SOCl$_2$/DMF/CHCl$_3$
3) NaN$_3$/acetone/H$_2$O
4) Ph$_2$O/Δ
5) POCl$_3$ then Δ

1) KOH/PhOH
2) NH$_4$OAc
3) P on
4 H$_2$/Pd(C)

Synthesis of 2-amino-1-H-pyrrolo[3,2-c]pyridine in which the 4-position may be a protected amine could be accomplished starting from the commercially available pyrrole-2-carboxaldehyde. Nitration and protection of pyrrole nitrogen with P1 would afford the nitro/aldehyde intermediate. Using literature methods (J. Med. Chem. 1989, 32, 1147) one could obtain the 2-nitro-4-chloro-pyrrolo[3,2-c] pyridine. Displacement of the 4-chloro with phenoxide then conversion to 4-amino followed by suitable protection and reduction of the aryl nitro group would provide the desired compound.

BOC-Protected aminobenzisoxazolemethylbromide can be reacted with the lithium salt of acetonitrile to give the nitrile. The nitrile can be further reacted in a similar fashion as in WO96/16940 to give the desired compound.

The compounds of the present invention have a group "A—B" attached to ring M. Preparations of some of the rings M and the "A—B" moieties can follow the same methods described in WO97/23212, WO97/30971, WO97/38984, WO98/01428, WO98/06694, WO98/28269, WO98/28282, WO98/57934, WO98/57937, and WO98/57951, the contents of which are incorporated herein by reference. Preparations of the some of the rings M can also follow the same methods described in WO98/28269, WO98/57951, and WO98/57937, the contents of which are incorporated herein by reference. Compounds of Formula I can be prepared by reacting an appropriate 6-5 system described above with an appropriate intermediate to either form the desired ring M or to be attached to desired ring M. The above noted publications describe conditions for coupling ring M and a desired 6-5 system.

Other features of the invention will become apparent in the course of the following descriptions of exemplary embodiments which are given for illustration of the invention and are not intended to be limiting thereof.

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa, thrombin, or both.

The effectiveness of compounds of the present invention as inhibitors of factor Xa can be determined using purified human factor Xa and synthetic substrate. The rate of factor Xa hydrolysis of chromogenic substrate S2222 (Kabi Pharmacia, Franklin, Ohio) can be measured both in the absence and presence of compounds of the present invention. Hydrolysis of the substrate resulted in the release of pNA, which can be monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis can be determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship can be used to calculate $K_i$ values:

$$(v_o-v_s)/v_s = I/(K_i(1+S/K_m))$$

where:
$v_o$ is the velocity of the control in the absence of inhibitor;
$v_s$ is the velocity in the presence of inhibitor;
I is the concentration of inhibitor;
$K_i$ is the dissociation constant of the enzyme:inhibitor complex;
S is the concentration of substrate;
$K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Compounds of the present invention can be shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) can be monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, can be incubated with various substrate concentrations ranging from 0.20 to 0.02 mM. After 25 to 30 minutes of incubation, thrombin activity can be assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

The compounds of the present invention can be administered alone or in combination with one or more additional therapeutic agents. These include other anticoagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and EP 293 881 A2, the disclosures of which are hereby incorporated herein by reference. Other suitable boroarginine derivatives and boropeptide thrombin inhibitors include those disclosed in WO92/07869 and EP 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdernal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The following tables contain representative examples of the present invention. Each entry in each table is intended to be paired with each formulae at the start of the table. For example, example 1 of Table 1 is intended to be paired with each of the formulae shown in Table 1. Example 1 of Table 2 is intended to be paired with each of the formulae shown in Table 2.

The following nomenclature is intended for group A in the following tables.

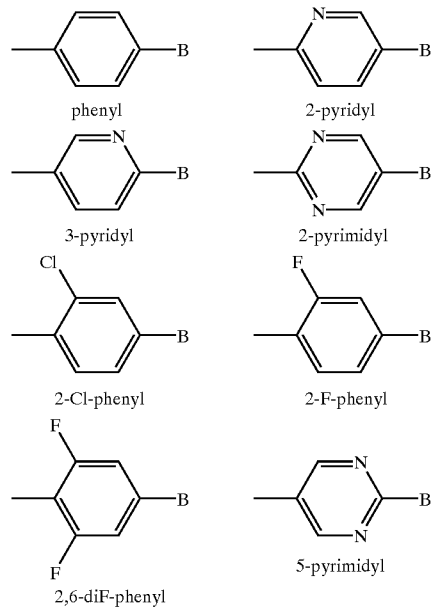

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula I:

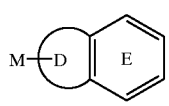

ring D is selected from —(CH$_2$)$_3$—, —CH$_2$CH=CH—, —CH$_2$N=CH—, and a 5 membered aromatic system containing from 0–2 heteroatoms selected from the group N, O, and S, provided that from 0–1 O and S atoms are present;

ring D is substituted with 0–2 R, provided that when ring D is unsubstituted, it contains at least one heteroatom;

E is phenyl substituted with 0–1 R;

R is selected from Cl, F, Br, I, OH, C$_{1-3}$ alkoxy, NH$_2$, NH(C$_{1-3}$ alkyl), N(C$_{1-3}$ alkyl)$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH(C$_{1-3}$ alkyl), and CH$_2$CH$_2$N(C$_{1-3}$ alkyl)$_2$;

M is selected from the group:

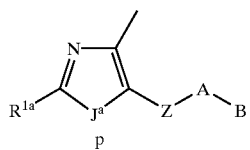

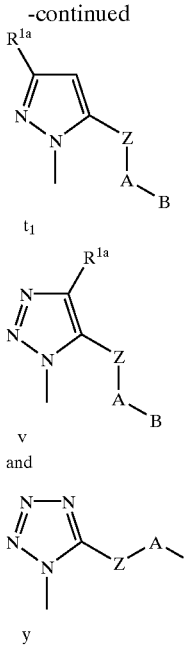

$J^a$ is NH or NR$^{1a}$;

Z is selected from (CR$^8$R$^9$)$_{1-4}$, (CR$^8$R$^9$)$_r$O(CR$^8$R$^9$)$_r$, (CR$^8$R$^9$)$_r$NR$^3$(CR$^8$R$^9$)$_r$, (CR$^8$R$^9$)$_r$C(O)(CR$^8$R$^9$)$_r$, (CR$^8$R$^9$)$_r$C(O)O(CR$^8$R$^9$)$_r$, (CR$^8$R$^9$)$_r$OC(O)(CR$^8$R$^9$)$_r$, (CR$^8$R$^9$)$_r$C(O)NR$^3$(CR$^8$R$^9$)$_r$, (CR$^8$R$^9$)$_r$NR$^3$C(O)(CR$^8$R$^9$)$_r$, (CR$^8$R$^9$)$_r$OC(O)O(CR$^8$R$^9$)$_r$, (CH$_2$)$_r$OC(O)NR$^3$(CR$^8$R$^9$)$_r$, (CR$^8$R$^9$)$_r$NR$^3$C(O)O(CR$^8$R$^9$)$_r$, (CH$_2$)$_r$NR$^3$C(O)NR$^3$(CR$^8$R$^9$)$_r$, (CR$^8$R$^9$)$_r$S(O)$_p$(CR$^8$R$^9$)$_r$, (CCR$^8$R$^9$)$_r$SO$_2$NR$^3$(CR$^8$R$^9$)$_r$, (CR$^8$R$^9$)$_r$NR$^3$SO$_2$(CR$^8$R$^9$)$_r$, and (CR$^8$R$^9$)$_r$NR$^3$SO$_2$NR$^3$(CR$^8$R$^9$)$_r$, provided that Z does not form a N—N, N—O, N—S, NCH$_2$N, NCH$_2$O, or NCH$_2$S bond with the groups to which Z is attached;

R$^{1a}$ is selected from H, —(CH$_2$)$_r$—R$^{1'}$, —CH=CH—R$^{1'}$, NHCH$_2$R$^{1''}$, OCH$_2$R$^{1''}$, SCH$_2$R$^{1''}$, NH(CH$_2$)$_2$(CH$_2$)$_t$R$^{1'}$, O(CH$_2$)$_2$(CH$_2$)$_t$R$^{1'}$, and S(CH$_2$)$_2$(CH$_2$)$_t$R$^{1'}$;

R$^{1'}$ is selected from H, C$_{1-3}$ alkyl, F, Cl, Br, I, —CN, —CHO, (CF2)$_r$CF$_3$, (CH$_2$)$_r$OR$^2$, NR$^2$R$^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, C(=NR$^{2c}$)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocycle substituted with 0–2 R$^4$, and 5–10 membered heterocycle containing from 1–4 heteroatoms selected from the group consisting of N, O, and S substituted with 0–2 R$^4$;

R$^{1''}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$;

R$^2$, at each occurrence, is selected from H, CF$_3$, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, C$_{3-6}$ cycloalkylmethyl substituted with 0–2 R$^{4b}$, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocycle substituted with 0–2 R$^{4b}$, and 5–6 membered heterocycle containing from 1–4 heteroatoms selected from the group consisting of N, O, and S substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

R$^3$, at each occurrence, is selected from H, C$_{1-4}$ alkyl, and phenyl;

R$^{3a}$, at each occurrence, is selected from H, C$_{1-4}$ alkyl, and phenyl;

R$^{3b}$, at each occurrence, is selected from H, C$_{1-4}$ alkyl, and phenyl;

R$^{3c}$, at each occurrence, is selected from C$_{1-4}$ alkyl, and phenyl;

A is selected from:
C$_{3-10}$ carbocycle substituted with 0–2 R$^4$, and
5–10 membered heterocycle containing from 1–4 heteroatoms selected from the group consisting of N, O, and S substituted with 0–2 R$^4$;

B is selected from:
H, Y, X—Y, NR$^2$R$^{2a}$, and C(=NR$^2$)NR$^2$R$^{2a}$, NR$^2$C(=NR$^2$)NR$^2$R$^{2a}$;

X is selected from C$_{1-4}$ alkylene, —CR$^2$(CR$^2$R$^{2b}$)(CH$_2$)$_t$—, —C(O)—, —C(=NR$^{1''}$)—, —CR$^2$(NR$^{1''}$R$^2$)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S(O)$_2$—, —NR$^2$S(O)$_2$CR$^2$R$^{2a}$—, —CR$^2$R$^{2a}$S(O)$_2$NR$^2$—, —NR$^2$S(O)$_2$NR$^2$—, —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)O—, —OC(O)NR$^2$—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from:
(CH$_2$)$_r$NR$^2$R$^{2a}$, provided that X—Y do not form a N—N, O—N, or S—N bond,
C$_{3-10}$ carbocycle substituted with 0–2 R$^{4a}$, and
5–10 membered heterocycle containing from 1–4 heteroatoms selected from the group consisting of N, O, and S substituted with 0–2 R$^{4a}$;

R$^4$, at each occurrence, is selected from H, =O, (CH$_2$)$_r$OR$^2$, F, Cl, Br, I, C$_{1-4}$ alkyl, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, C(=NR$^2$)NR$^2$R$^{2a}$, C(=NS(O)$_2$R$^5$) NR$^2$R$^{2a}$, NHC(=NR$^2$)NR$^2$R$^{2a}$, C(O)NHC(=NR$^2$) NR$^2$R$^{2a}$, SO$_2$NR$^2$R$^{2a}$, NR$^2$SO$_2$NR$^2$R$^{2a}$, NR$^2$SO$_2$— C$_{1-4}$ alkyl, NR$^2$SO$_2$R$^5$, S(O)$_p$R$^5$, (CF$_2$)$_r$CF$_3$, NHCH$_2$R$^{1''}$, OCH$_2$R$^{1''}$, SCH$_2$R$^{1''}$, N(CH$_2$)$_2$(CH$_2$)$_t$R$^{1''}$, O(CH$_2$)$_2$(CH$_2$)$_t$R$^{1''}$, and S(CH$_2$)$_2$(CH$_2$)$_t$R$^{1''}$, alternatively, one R$^4$ is a 5–6 membered aromatic heterocycle containing from 1–4 heteroatoms selected from the group consisting of N, O, and S;

R$^{4a}$, at each occurrence, is selected from H, =O, (CH$_2$)$_r$ OR$^2$, (CH$_2$)$_r$—F, (CH$_2$)$_r$—Br, (CH$_2$)$_r$—Cl, Cl, Br, F, I, C$_{1-4}$ alkyl, —CN, NO$_2$, (CH$_2$)$_r$NR$^2$R$^{2a}$, (CH$_2$)$_r$C(O) R$^{2c}$, NR$^2$C(O)R$^{2b}$, C(O)NR$^2$R$^{2a}$, C(O)NH(CH$_2$)

$_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, =O, $(CH_2)_r$ $OR^3$, F, Cl, Br, I, $C_{1-4}$ alkyl, —CN, $NO_2$, $(CH_2)_r$ $NR^3R^{3a}$, $(CH_2)_rC(O)R^3$, $(CH_2)_rC(O)OR^{3c}$, $NR^3C(O)$ $R^{3a}$, $C(O)NR^3R^{3a}$, $NR^3C(O)NR^3R^{3a}$, $C(=NR^3)$ $NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_r$ $OR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)$ $NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

R9, at each occurrence, is selected from H, $C_{1-6}$ alkyl and $(CH_2)_n$-phenyl;

n, at each occurrence, is selected from 0, 1, 2, and 3;

m, at each occurrence, is selected from 0, 1, and 2;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0, 1, 2, and 3.

2. A compound according to claim 1, wherein:

Z is selected from $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$, $SO_2NH$, and $NHSO_2$, provided that Z does not form a N—N, N—O, $NCH_2N$, or $NCH_2O$ bond with ring M or group A;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: H, Y, and X—Y;

X is selected from $C_{1-4}$ alkylene, —C(O)—, —C(=NR)—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is $NR^2R^{2a}$ or $CH_2NR^2R^{2a}$, provided that X—Y do not form a N—N or O—N bond;

alternatively, Y is selected from one of the following carbocyclic and heterocyclic systems which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

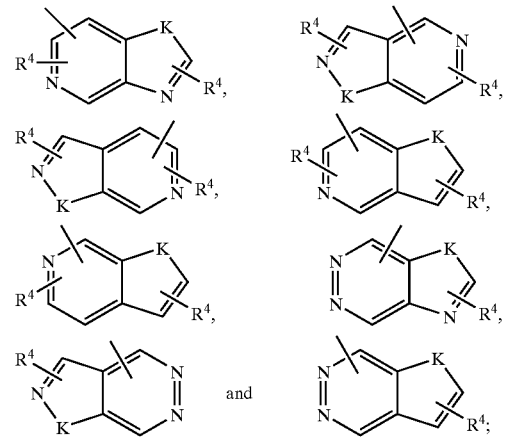

K is selected from O, S, NH, and N.

3. A compound according to claim 2, wherein:

Z is $C(O)CH_2$ and CONH, provided that Z does not form a N—N bond with group A;

A is selected from phenyl, pyridyl, and pyrimidyl, and is substituted with 0–2 $R^4$; and, B is selected from Y, X—Y, phenyl, pyrrolidino, morpholino, 1,2,3-triazolyl, and imidazolyl, and is substituted with 0–1 $R^{4a}$;

X is selected from $CH_2$, —C(O)—, and O;

Y is $NR^2R^{2a}$ or $CH_2NR^2R^{2a}$, provided that X—Y does not form an O—N bond;

alternatively, Y is selected from one of the following carbocyclic and heterocyclic systems which are substituted with 0–2 $R^{4a}$;

phenyl, piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, $CH(CH_3)_2$, cyclopropylmethyl, benzyl, and phenyl;

alternatively, $R^2$ and $R^{2a}$ combine to form a ring system substituted with 0–2 $R^{4b}$, the ring system being selected from pyrrolidinyl, piperazinyl and morpholino;

$R^4$, at each occurrence, is selected from OH, $(CH_2)_rOR^2$, Cl, F, $C_{1-4}$ alkyl, $(CH_2)_rNR^2R^{2a}$, and $(CF_2)_rCF_3$;

$R^{4a}$ is selected from Cl, F, $C_{1-4}$ alkyl, $CF_3$, $(CH_2)_r$ $NR^2R^{2a}$, $S(O)_pR^5$, $SO_2NR^2R^{2a}$, and 1-$CF_3$-tetrazol-2-yl;

$R^{4b}$, at each occurrence, is selected from OH, Cl, F, $CH_3$, and $CF_3$;

$R^5$, at each occurrence, is selected from $CF_3$, $C_{1-6}$ alkyl, phenyl, and benzyl;

$R^7$, at each occurrence, is selected from H, $CH_3$, and $CH_2CH_3$; and, $R^8$, at each occurrence, is selected from H and $CH_3$.

4. A compound according to claim 3, wherein:

$R^{1a}$ is absent or is —$(CH_2)_r$—$R^{1'}$;

$R^{1'}$ is selected from H, $C_{1-3}$ alkyl, F, Cl, —CN, $CF_3$, $(CH_2)_rOR^2$, $NR^2R^{2a}$, $C(O)R^{2c}$, $OC(O)R^2$, $S(O)_pR^{2b}$, $NR^2C(O)R^{2b}$, $C(O)NR^2R^{2a}$, $SO_2NR^2R^{2a}$, $C_{3-6}$ carbocycle substituted with 0–2 $R^{4a}$, and 5–6 membered heterocycle containing from 1–4 heteroatoms selected from the group consisting of N, O, and S substituted with 0–2 $R^{4a}$;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl) phenyl, 2-(dimethylaminosulfonyl)phenyl, 1-pyrrolidinocarbonyl, 2-(methylsulfonyl)phenyl, 2-(N,N-dimethylaminomethyl)phenyl, 2-(isopropylaminomethyl)phenyl, 2-(cyclopropylaminomethyl)phenyl, 2-(N-pyrrolidinylmethyl)phenyl, 2-(3-hydroxy-N-pyrrolidinylmethyl)phenyl, 4-morpholino, 2-(1'-$CF_3$-tetrazol-2-yl)phenyl, 4-morpholinocarbonyl, 1-methyl-2-imidazolyl, 2-methyl-1-imidazolyl, 5-methyl-1-imidazolyl, 2-(N,N-dimethylaminomethyl)imidazolyl, 2-methylsulfonyl-1-imidazolyl and, 5-methyl-1,2,3-triazolyl.

5. A pharmaceutical composition, comprising: a pharmaceutically acceptable carrier and a therapeutically effective amount of a compound according to claim 1 or a pharmaceutically acceptable salt thereof.

6. A pharmaceutical composition, comprising: a pharmaceutically acceptable carrier and a therapeutically effective amount of a compound according to claim 2 or a pharmaceutically acceptable salt thereof.

7. A pharmaceutical composition, comprising: a pharmaceutically acceptable carrier and a therapeutically effective amount of a compound according to claim 3 or a pharmaceutically acceptable salt thereof.

8. A pharmaceutical composition, comprising: a pharmaceutically acceptable carrier and a therapeutically effective amount of a compound according to claim 4 or a pharmaceutically acceptable salt thereof.

9. A method for treating a thromboembolic disorder, comprising: administering to a patient in need thereof a therapeutically effective amount of a compound according to claim 1 or a pharmaceutically acceptable salt thereof.

10. A method for treating a thromboembolic disorder, comprising: administering to a patient in need thereof a therapeutically effective amount of a compound according to claim 2 or a pharmaceutically acceptable salt thereof.

11. A method for treating a thromboembolic disorder, comprising: administering to a patient in need thereof a therapeutically effective amount of a compound according to claim 3 or a pharmaceutically acceptable salt thereof.

12. A method for treating a thromboembolic disorder, comprising: administering to a patient in need thereof a therapeutically effective amount of a compound according to claim 4 or a pharmaceutically acceptable salt thereof.

13. A method according to claim 9, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

14. A method according to claim 10, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

15. A method according to claim 11, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

16. A method according to claim 12, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

* * * * *